United States Patent
Lee et al.

(10) Patent No.: US 11,070,924 B2
(45) Date of Patent: Jul. 20, 2021

(54) METHOD AND APPARATUS FOR HEARING IMPROVEMENT BASED ON COCHLEAR MODEL

(71) Applicant: GOLDENEAR COMPANY, INC., Valencia, CA (US)

(72) Inventors: Daehee Lee, Valencia, CA (US); Sangyeop Kwak, Valencia, CA (US); Sungshin Jang, Valencia, CA (US)

(73) Assignee: GOLDENEAR COMPANY, INC., Valencia, CA (US)

( * ) Notice: Subject to any disclaimer, the term of this patent is extended or adjusted under 35 U.S.C. 154(b) by 0 days.

(21) Appl. No.: 17/093,787

(22) Filed: Nov. 10, 2020

(65) Prior Publication Data

US 2021/0168520 A1 Jun. 3, 2021

Related U.S. Application Data

(60) Provisional application No. 62/974,353, filed on Nov. 29, 2019.

(51) Int. Cl.
*H04R 25/00* (2006.01)
*A61B 5/12* (2006.01)
*A61N 1/36* (2006.01)

(52) U.S. Cl.
CPC ............ *H04R 25/50* (2013.01); *A61B 5/121* (2013.01); *A61N 1/36038* (2017.08); *H04R 25/70* (2013.01)

(58) Field of Classification Search
None
See application file for complete search history.

(56) References Cited

U.S. PATENT DOCUMENTS

| 5,664,577 A * | 9/1997 | Lonsbury-Martin .... A61B 5/12 600/559 |
|---|---|---|
| 2004/0028250 A1* | 2/2004 | Shim ..................... H04R 25/70 381/312 |
| 2008/0228101 A1* | 9/2008 | Allen ..................... A61B 5/411 600/559 |
| 2011/0238176 A1* | 9/2011 | Bradley ............... A61N 1/0541 623/10 |
| 2015/0088225 A1* | 3/2015 | Noble ..................... G06T 7/149 607/57 |
| 2015/0281857 A1* | 10/2015 | Hau ..................... H04R 25/353 381/317 |
| 2016/0175591 A1* | 6/2016 | Chaiupper ............... A61B 5/16 607/3 |
| 2016/0279414 A1* | 9/2016 | Schleich ............ A61N 1/36039 |
| 2017/0072197 A1* | 3/2017 | Alfsmann ............ H04R 25/353 |

(Continued)

*Primary Examiner* — Harry S Hong

(57) ABSTRACT

There is provided an apparatus for hearing measurement based on a cochlear model comprising: a processor; and a memory connected to the processor, wherein the memory stores program instructions executable by the processor to output an interface in which n buttons corresponding to n frequency bands into which an audible frequency band is divided at 1/k octave resolution are arranged in a cochlear model, output acoustic signals corresponding to a predetermined hearing threshold in each of the n frequency bands, receive a user's input for whether each of the n frequency bands is inaudible at the predetermined hearing threshold, and output acoustic stimulation signals corresponding to the inaudible frequency band input by the user in predetermined sizes.

10 Claims, 5 Drawing Sheets

(56) References Cited

U.S. PATENT DOCUMENTS

| | | | | |
|---|---|---|---|---|
| 2017/0300292 A1* | 10/2017 | Torrini | ................. | G06F 3/0482 |
| 2018/0015287 A1* | 1/2018 | Heasman | ........... | A61N 1/36036 |
| 2020/0054877 A1* | 2/2020 | Calixto | ............. | A61N 1/36132 |

* cited by examiner

FIG. 5

| Activation Record | | | | | |
|---|---|---|---|---|---|
| Date | TSC Level | Score | | | Time |
| | | Left | Right | Total | |
| 02-20-2019 11:03:16 | 10 | 68 | 62 | 65 | 0:03 |
| 02-20-2019 11:02:23 | 20 | 75 | 71 | 73 | 0:03 |
| 02-20-2019 11:01:36 | 30 | 88 | 88 | 88 | 0:05 |
| 02-20-2019 11:00:54 | 10 | 88 | 84 | 86 | 0:03 |
| 02-20-2019 10:59:57 | 40 | 94 | 94 | 94 | 0:05 |

View All >

METHOD AND APPARATUS FOR HEARING IMPROVEMENT BASED ON COCHLEAR MODEL

CROSS-REFERENCE TO RELATED APPLICATIONS

This application claims the benefit of U.S. Provisional Application Ser. No. 62/974,353, entitled "HEARING TEST TEMPLATE AND METHOD TO USE, CLASSIFY AND ANALYZE DATA ON HEARING TEST RESULTS AND HEARING IMPROVEMENT RESULTS" and filed on Nov. 30, 2019, which is expressly incorporated herein by reference in its entirety.

BACKGROUND

(a) Technical Field

The present invention relates to a method and an apparatus for hearing improvement based on a cochlear model.

(b) Background Art

All organs that transmit sound to the brain are collectively called the auditory organ.

The auditory organ is largely divided into the outer ear, the middle ear, and the inner ear, and the sound introduced from the outside through the outer ear vibrates in the eardrum and is transmitted to the cochlea of the inner ear through the middle ear.

Hair cells of cochlea are arranged in the basilar membrane of the cochlea, and the total number of the hair cells of cochlea arranged uniformly on the basilar membrane is approximately 12,000. The length of the basilar membrane is approximately 2.5 to 3 cm, and the hair cells of cochlea located at the starting part of the basilar membrane sense high frequencies, and the hair cells of cochlea located at the end of the basilar membrane sense low frequencies.

This is called frequency specificity of the hair cells of cochlea, and the frequency specificity resolution at the most ideal stimulation intensity level is known to reach a range of approximately 0.2 mm (0.5 semitone) on the basilar membrane.

Meanwhile, in recent years, many people have sensorineural hearing loss diseases due to the increased use of portable audio devices and exposure to various noises. The sensorineural hearing loss is the hearing degradation caused by damage to the hair cells of cochlea, and is caused by aging, noise exposure, drug side effects, and genetic factors.

The sensorineural hearing loss is classified into mild, moderate, severe, and deep hearing loss according to the degree of hearing impairment, and in general, ordinary conversation is difficult with moderate hearing loss or higher.

Currently, it has been estimated that about 10% of the world's population has mild hearing loss symptoms enough to feel their own hearing degeneration, and it has been estimated that the scale of patients with severe hearing loss of moderate or higher is approximately 260 million or more only in developing countries.

In the related art, a method for treating hearing loss diseases has not been introduced, but only a hearing aid is provided as a hearing aid related to hearing loss.

The hearing aid is a device that simply amplifies external sounds to hear the sounds loudly, but does not fundamentally prevent the hearing degeneration, but rather has a problem of further degenerating the hearing of a hearing aid user due to the amplified sound.

Therefore, there is an urgent need for a method capable of fundamentally treating hearing loss diseases rather than using the hearing aid.

In addition, in addition to the hearing loss, recently, interest in the treatment of tinnitus, which feels sound even without external stimuli, has increased.

The present applicant has already confirmed that for treatment of hearing loss and tinnitus, acoustic stimulation signals (modulated acoustic signals) are provided in a frequency band corresponding to damaged hair cells of cochlea to treat the hearing loss and tinnitus.

However, in the conventional method, since a hearing threshold is determined for each frequency band to be measured, when there are many frequency bands, there is a problem that it takes too long time to measure the user's hearing.

Therefore, there is a need for a method for solving such problems.

The above information disclosed in this Background section is only for enhancement of understanding of the background of the invention and therefore it may contain information that does not form the prior art that is already known in this country to a person of ordinary skill in the art.

SUMMARY OF THE DISCLOSURE

The present disclosure has been made in an effort to solve the above-described problems associated with prior art. An object of the present disclosure is to provide a method and an apparatus for hearing improvement based on a cochlear model capable of rapidly determining a hearing threshold for each frequency band for hearing improvement.

The objects of the present disclosure are not limited to the aforementioned objects, and other objects, which are not mentioned above, will be apparently understood to those skilled in the art from the following description.

In order to achieve the objects described above, according to an embodiment of the present disclosure, there is provided an apparatus for hearing measurement based on a cochlear model comprising: a processor; and a memory connected to the processor, wherein the memory stores program instructions executable by the processor to output an interface in which n buttons corresponding to n frequency bands into which an audible frequency band is divided at 1/k octave resolution are arranged in a cochlear model, output acoustic signals corresponding to a predetermined hearing threshold in each of the n frequency bands, receive a user's input for whether each of the n frequency bands is inaudible at the predetermined hearing threshold, and output acoustic stimulation signals corresponding to the inaudible frequency band input by the user in predetermined sizes.

The interface may include a hearing threshold button for selecting the hearing threshold, an inaudible button for selecting when an acoustic signal corresponding to the predetermined hearing threshold is not heard, and an activation button for outputting the acoustic stimulation signal.

The hearing threshold may be selected by the user or automatically selected according to a user's age.

The program instructions may control the buttons corresponding to the measured frequency band, the non-measured frequency band, and the inaudible frequency band to be displayed in different colors.

The program instructions may display the n buttons in a first color at the time of initial measurement, change a first button to a second color when the first button of the n buttons is selected, and change the first button to a third color when the user selects the inaudible button while the acoustic signal in the frequency band corresponding to the first button is output.

The program instructions may output acoustic stimulation signals corresponding to first and m-th frequency bands among a plurality of m adjacent frequency bands to each other when the inaudible frequency band includes m adjacent frequency bands to each other.

The acoustic stimulation signal may have a size equal to or smaller than the hearing threshold provided at the time of measurement.

The program instructions may determine the number of buttons corresponding to the inaudible frequency band at the predetermined hearing threshold to change the predetermined hearing threshold to another hearing threshold.

According to another aspect of the present disclosure, there is provided a method for improving hearing in an apparatus including a processor and a memory connected to the processor, comprising: outputting an interface in which n buttons corresponding to n frequency bands into which an audible frequency band is divided at 1/k octave resolution are arranged in a cochlear model; outputting acoustic signals corresponding to a predetermined hearing threshold in each of then frequency bands; receiving a user's input for whether each of the n frequency bands is inaudible at the predetermined hearing threshold; and outputting acoustic stimulation signals corresponding to the inaudible frequency band input by the user in predetermined sizes.

According to yet another aspect of the present disclosure, there is provided a program for performing the method.

According to the present disclosure, one threshold sound conditioning (TSC) level is pre-selected to determine a Y value corresponding to the pre-selected hearing threshold as a preliminary constant Y', and a user selects only a frequency band (X values) that are inaudible in all the frequency bands where hearing is to be measured, and thus, there are advantages of measuring hearing more quickly and attempting accurate hearing improvement.

The effects of the present disclosure are not limited to the aforementioned effect, and other effects, which are not mentioned above, will be apparently understood to those skilled in the art from the description of the appended claims.

BRIEF DESCRIPTION OF THE DRAWINGS

The above and other features of the present disclosure will now be described in detail with reference to certain exemplary embodiments thereof illustrated the accompanying drawings which are given hereinbelow by way of illustration only, and thus are not limitative of the present disclosure, and wherein:

FIG. 5 is a diagram illustrating a hearing measurement result according to the present embodiment;

Figure 1:
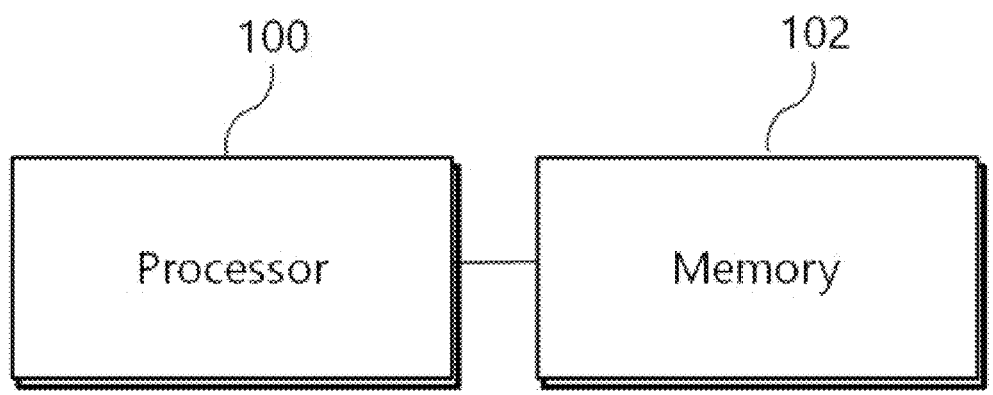
FIG. 1 is a diagram illustrating a configuration of an apparatus for hearing improvement based on a cochlear model according to an embodiment of the present disclosure.

It should be understood that the appended drawings are not necessarily to scale, presenting a somewhat simplified representation of various preferred features illustrative of the basic principles of the invention. The specific design features of the present disclosure as disclosed herein, including, for example, specific dimensions, orientations, locations, and shapes will be determined in part by the particular intended application and use environment.

In the figures, reference numbers refer to the same or equivalent parts of the present disclosure throughout the several figures of the drawing.

DETAILED DESCRIPTION

The present disclosure may have various modifications and various embodiments and specific embodiments will be illustrated in the drawings and will be described in detail. However, the present disclosure is not limited to specific embodiments, and it should be understood that the present disclosure covers all modifications, equivalents and replacements included within the idea and technical scope of the present disclosure. In describing each drawing, like reference numerals have been used for like components.

It should be understood that, when it is described that a component is "connected to" or "access" the other component, the component may be directly connected to or access the other component or another component may be present therebetween. In contrast, it should be understood that, when it is described that a component is "directly connected to" or "directly access" the other component, it will be understood that another component is not present therebetween.

Terms used in the present application are used only to describe specific embodiments, and are not intended to limit the present disclosure. A singular form may include a plural form unless otherwise clearly meant in the context. In the present application, it should be understood that the term "comprising", "including", or "having" indicates that a feature, a number, a step, an operation, a component, a part or a combination thereof described in the specification is present, but does not exclude a possibility of presence or addition of one or more other features, numbers, steps, operations, components, parts or combinations thereof, in advance.

Unless contrarily defined, all terms used herein including technological or scientific terms have the same meanings as those generally understood by a person with ordinary skill in the art. Terms which are defined in a generally used dictionary should be interpreted to have the same meaning as the meaning in the context of the related art, and are not interpreted as an ideal meaning or excessively formal meanings unless clearly defined in the present application.

Hereinafter, a preferable embodiment of the present disclosure will be described in detail with reference to the accompanying drawings. In describing the present disclosure, like reference numerals will be used for like means regardless of the drawing number in order to facilitate an overall understanding.

FIG. 1 is a diagram illustrating a configuration of an apparatus for hearing improvement based on a cochlear model according to an embodiment of the present disclosure.

The apparatus according to the present embodiment is an apparatus that outputs an interface for measuring hearing and acoustic signals, receives a user's input, and outputs acoustic stimulation signals for improving user's hearing, and may include all of a typical desktop, a notebook, a touch pad and a mobile phone.

As illustrated in FIG. 1, the apparatus for hearing improvement according to the present embodiment may include a processor 100 and a memory 102.

The processor 100 may include a central processing unit (CPU) capable of executing a computer program, other virtual machines, or the like.

The memory 102 may include a nonvolatile storage device such as a fixed hard drive or a detachable storage device. The detachable storage device may include a compact flash unit, a USB memory stick, etc. The memory 102 may also include volatile memories such as various types of random access memories.

According to an embodiment of the present disclosure, the processor 100 determines a frequency band requiring improvement of the user by using program instructions stored in the memory 102, and provides an acoustic stimulation signal for stimulating hair cells of cochlea for the determined frequency band.

The program instructions according to the present embodiment output an interface in which n buttons corresponding to n frequency bands where an audible frequency band is divided at 1/k octave resolution are disposed in a cochlear model, outputs an acoustic signal corresponding to a predetermined hearing threshold in each of the n frequency bands, receives a user's input for whether it is inaudible in each of the n frequency bands at the predetermined hearing threshold, and outputs an acoustic stimulation signal corresponding to the inaudible frequency band input by the user.

Figure 2:
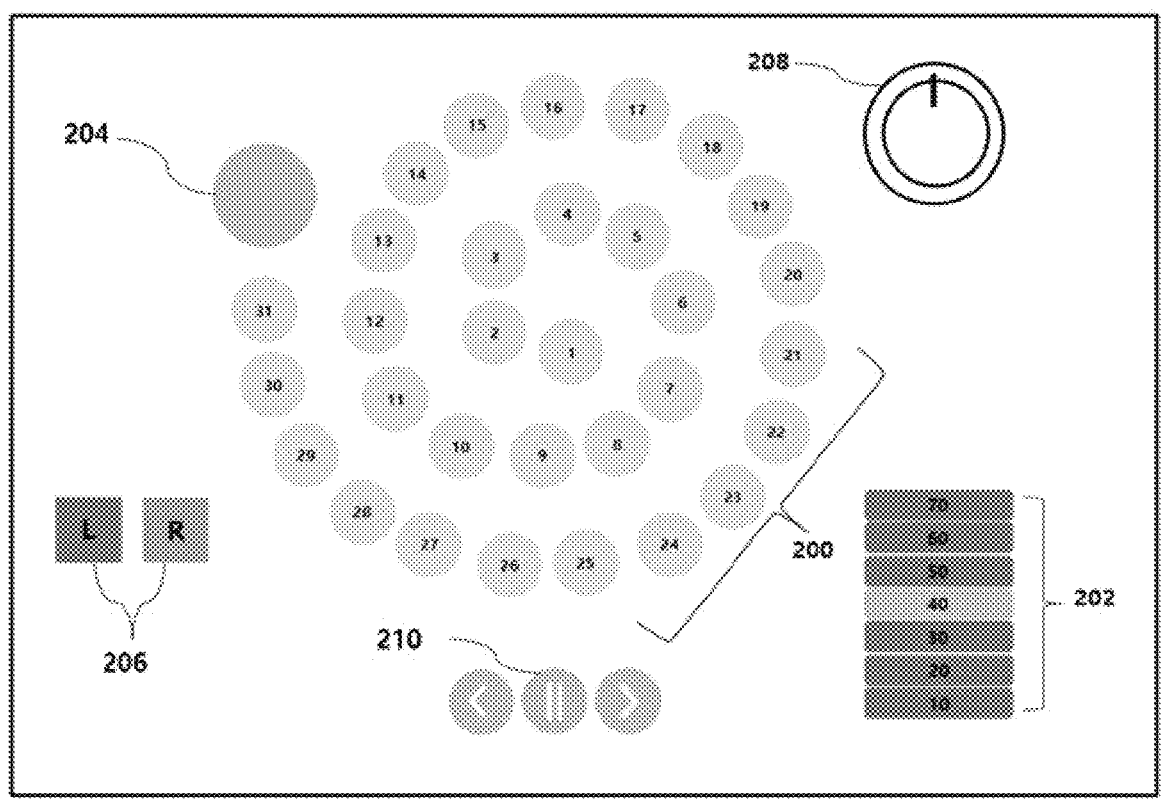
FIG. 2 is a diagram illustrating an interface for measuring and improving hearing according to a preferred embodiment of the present disclosure.

FIG. 2 is a diagram illustrating an interface for measuring and improving hearing according to a preferred embodiment of the present disclosure.

As illustrated in FIG. 2, the interface according to the present embodiment includes n buttons 200 corresponding to n frequency bands into which the audible frequency band is divided at 1/k octave resolution, a hearing threshold button 202, an inaudible button 204, left and right buttons 206, and an activation button 208.

The buttons included in the interface according to the present embodiment may be selected through a mouse or a user's touch input.

In FIG. 2, it is illustrated as an example that an audible frequency band to be measured is divided into 31 frequency bands, and the 31 frequency bands are set as shown in Table 1.

TABLE 1

| number | frequency [Hz] |
|---|---|
| [01] | 269~320 |
| [02] | 311~370 |
| [03] | 359~427 |
| [04] | 415~494 |
| [05] | 480~570 |

TABLE 1-continued

| number | frequency [Hz] |
|---|---|
| [06] | 554~659 |
| [07] | 640~762 |
| [08] | 740~880 |
| [09] | 855~1017 |
| [10] | 960~1142 |
| [11] | 1078~1281 |
| [12] | 1209~1438 |
| [13] | 1357~1614 |
| [14] | 1523~1812 |
| [15] | 1710~2034 |
| [16] | 1920~2282 |
| [17] | 2154~2562 |
| [18] | 2418~2876 |
| [19] | 2714~3228 |
| [20] | 3047~3623 |
| [21] | 3420~4067 |
| [22] | 3838~4565 |
| [23] | 4309~5124 |
| [24] | 4836~5752 |
| [25] | 5429~6456 |
| [26] | 6093~7246 |
| [27] | 6840~8134 |
| [28] | 7677~9130 |
| [29] | 8617~10248 |
| [30] | 9672~11503 |
| [31] | 10857~12912 |

Further, the n buttons according to the present embodiment are arranged in a cochlear model while having the following vector values (coordinate values).

TABLE 2

| number | Vector |
|---|---|
| [01] | top: 45.9%, left: 50.0% |
| [02] | top: 43.1%, left: 37.9% |
| [03] | top: 30.7%, left: 38.3% |
| [04] | top: 24.6%, left: 49.1% |
| [05] | top: 28.0%, left: 61.0% |
| [06] | top: 39.1%, left: 66.5% |
| [07] | top: 51.4%, left: 65.3% |
| [08] | top: 61.1%, left: 57.5% |
| [09] | top: 63.4%, left: 45.3% |
| [10] | top: 60.9%, left: 33.1% |
| [11] | top: 53.2%, left: 23.4% |
| [12] | top: 41.2%, left: 20.2% |
| [13] | top: 28.8%, left: 21.2% |
| [14] | top: 17.5%, left: 26.3% |
| [15] | top: 9.2%, left: 35.5% |
| [16] | top: 7.0%, left: 47.7% |
| [17] | top: 8.5%, left: 60.0% |
| [18] | top: 13.4%, left: 71.4% |
| [19] | top: 23.1%, left: 79.2% |
| [20] | top: 34.6%, left: 83.8% |
| [21] | top: 47.0%, left: 84.0% |
| [22] | top: 59.2%, left: 81.6% |
| [23] | top: 69.9%, left: 75.3% |
| [24] | top: 77.0%, left: 65.1% |
| [25] | top: 80.1%, left: 53.1% |
| [26] | top: 80.4%, left: 40.7% |
| [27] | top: 78.0%, left: 28.5% |
| [28] | top: 71.7%, left: 17.8% |
| [29] | top: 62.6%, left: 9.3% |
| [30] | top: 51.3%, left: 4.1% |
| [31] | top: 39.0%, left: 2.0% |

The hearing threshold button 202 is a button for the user to determine the size of an acoustic signal for hearing measurement. According to the present embodiment, a plurality of hearing threshold buttons having different sizes, such as 10 to 70 decibels, are included, and a size (measured hearing threshold) of the acoustic signal of each frequency band output when the user's hearing is measured may be selected by the user or automatically determined according to the user's age.

Hereinafter, for convenience of explanation, the size of the acoustic signal selected for hearing measurement selected by the user is defined as the hearing threshold in the interface illustrated in FIG. 2.

In the related art, the hearing threshold in the corresponding frequency band was measured while changing the size of the hearing threshold for each frequency band, but according to the present embodiment, the acoustic signal having the size corresponding to the hearing threshold selected by the user or automatically selected is output in the entire audible frequency band.

The acoustic signal for hearing measurement may be output when the user selects one of the n buttons or selects a play button 210 included in the interface.

During hearing measurement, the user hears an acoustic signal corresponding to a predetermined hearing threshold in each frequency band and determines whether it is inaudible. In the inaudible button 204, the number of the button corresponding to the frequency band to be currently measured is displayed, and if the acoustic signal is heard, the button moves to a next frequency band, and if not, the inaudible button 204 included in the interface is selected.

In the interface according to the present embodiment, buttons corresponding to the frequency band and the inaudible frequency band which have been measured are displayed to be identifiable in buttons arranged in a cochlear model.

Figure 3:
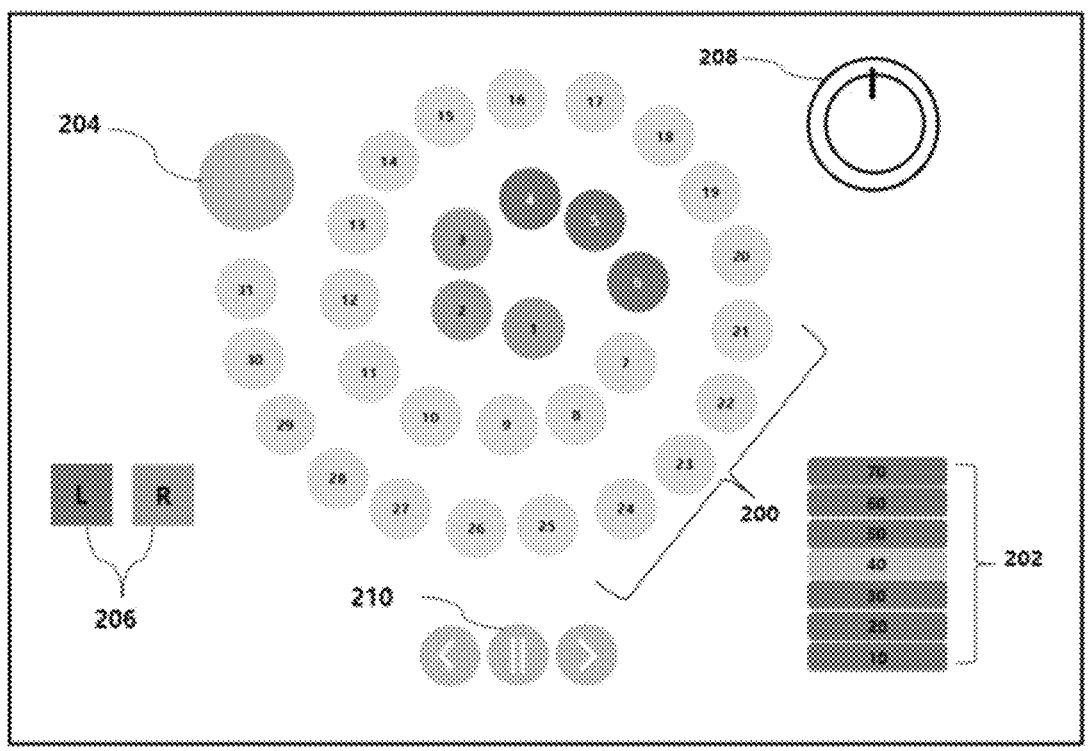
FIG. 3 is a diagram illustrating a change in interface when measuring the hearing according to the present embodiment.

FIG. 3 is a diagram illustrating a change in interface when measuring the hearing according to the present embodiment.

Referring to FIG. 3, in an initial state, n buttons are displayed in a first color, and then a button corresponding to a frequency band which has been measured by the user is changed to a second color.

In FIG. 3, it is assumed that acoustic signals corresponding to a predetermined hearing threshold are sequentially output from button 1.

When the user selects the inaudible button 204 because the acoustic signals output from buttons 4 to 6 are not heard, the colors of buttons 4 to 6 are changed to a third color.

Preferably, the first color, the second color, and the third color may be colors having different colors, brightness, and chroma.

The apparatus for hearing improvement according to the present embodiment stores information on a frequency band selected by the inaudible button 204.

After the measurement of either hearing is completed, the measurement of the other hearing is started through the input of the left and right buttons 206.

According to the present embodiment, when a preset number or higher of inaudible frequency bands is included when either hearing is measured, the size of the corresponding hearing threshold may not be appropriate in the user's hearing measurement. In this case, another hearing threshold is selected from the hearing threshold button 202 so that the hearing measurement may be performed again.

For example, when the user selects the inaudible button 204 *i* times or more (e.g., 5 times or more) while the hearing measurement is performed at 40 decibels, a predetermined message is output to allow the user to perform the hearing measurement again at a hearing threshold of 50 to 60 decibels.

More preferably, when the acoustic signal is not heard in a predetermined number of consecutive sections, the hearing threshold may be set higher by one or two levels to perform the hearing measurement.

In addition, even when none of the inaudible frequency bands are detected in a predetermined hearing threshold, that is, when acoustic signals are heard in all frequency bands, the predetermined hearing threshold may be inappropriate.

In this case, if there is a change in the user's hearing threshold, the apparatus for hearing improvement performs the hearing measurement again at a decibel lower by one level than the current hearing threshold.

When the left and right hearing measurement is completed, the activation button 208 included in the interface according to the present embodiment is displayed to be identifiable to the user in a flashing manner.

When the user selects the activation button 208, an acoustic stimulation signal for stimulating hair cells of cochlea in an inaudible frequency band is output in a predetermined size.

Preferably, the acoustic stimulation signal for stimulating the hair cells of cochlea may have a size equal to or smaller than the hearing threshold provided at the time of measurement.

Accordingly, the user may not be greatly disturbed while hearing the acoustic stimulation signal for stimulating the hair cells of cochlea.

When the inaudible frequency bands are not adjacent to each other, the acoustic stimulation signal corresponding to the individual frequency band is provided to stimulate the hair cells of cochlea.

On the other hand, when the inaudible frequency bands include a plurality of adjacent frequency bands to each other, the apparatus for hearing improvement according to the present embodiment outputs only acoustic stimulation signals corresponding to the first and m-th frequency bands among the plurality of m adjacent frequency bands to each other to stimulate the hair cells of cochlea.

According to the present embodiment, the acoustic stimulation signals in the inaudible frequency band may be simultaneously output in consideration of the left and right inaudible frequency bands.

Figure 4:
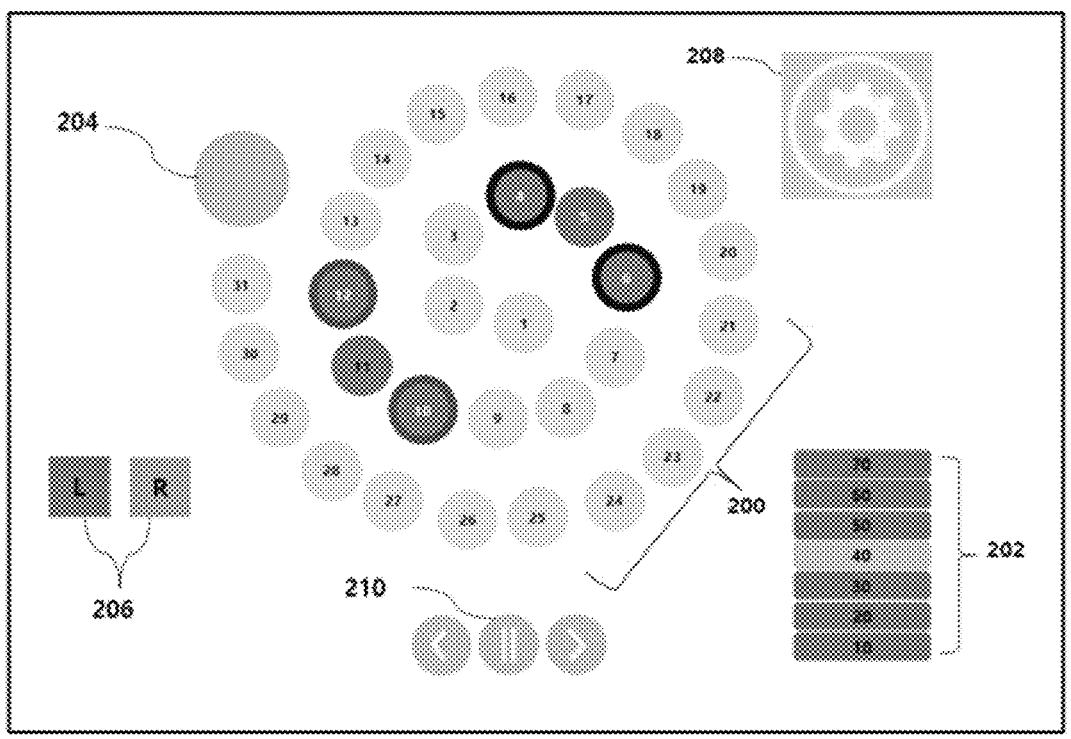
FIG. 4 is a diagram illustrating an output state of acoustic stimulation signals for stimulating hair cells of cochlea according to the present embodiment.

As illustrated in FIG. 4, when outputting the acoustic stimulation signal for stimulation of the hair cells of cochlea, the activation button 208 is changed differently, and when the acoustic stimulation signals in the inaudible frequency band are output, some of the n buttons are changed to different colors (buttons 4 and 6, 10 and 12) so that the user can identify the frequency bands in which the acoustic stimulation signals are output.

In addition, not only the color is changed, but also the background and shadow shapes of some buttons corresponding to the inaudible frequency bands may be changed to different colors.

The colors for the left ear (L) and the right ear (R) may be displayed separately, and when the inaudible frequency bands of the left ear (L) and the right ear (L) overlap with each other, the button of the overlapping frequency band may be displayed separately from others.

According to the present disclosure, it is possible to quickly measure a hearing threshold from a low frequency band to a high frequency band through a predefined hearing threshold in an intuitive cochlear model, and to improve the hearing by providing the acoustic stimulation signals for stimulation of hair cells of cochlea in inaudible frequency bands.

Figure 5:
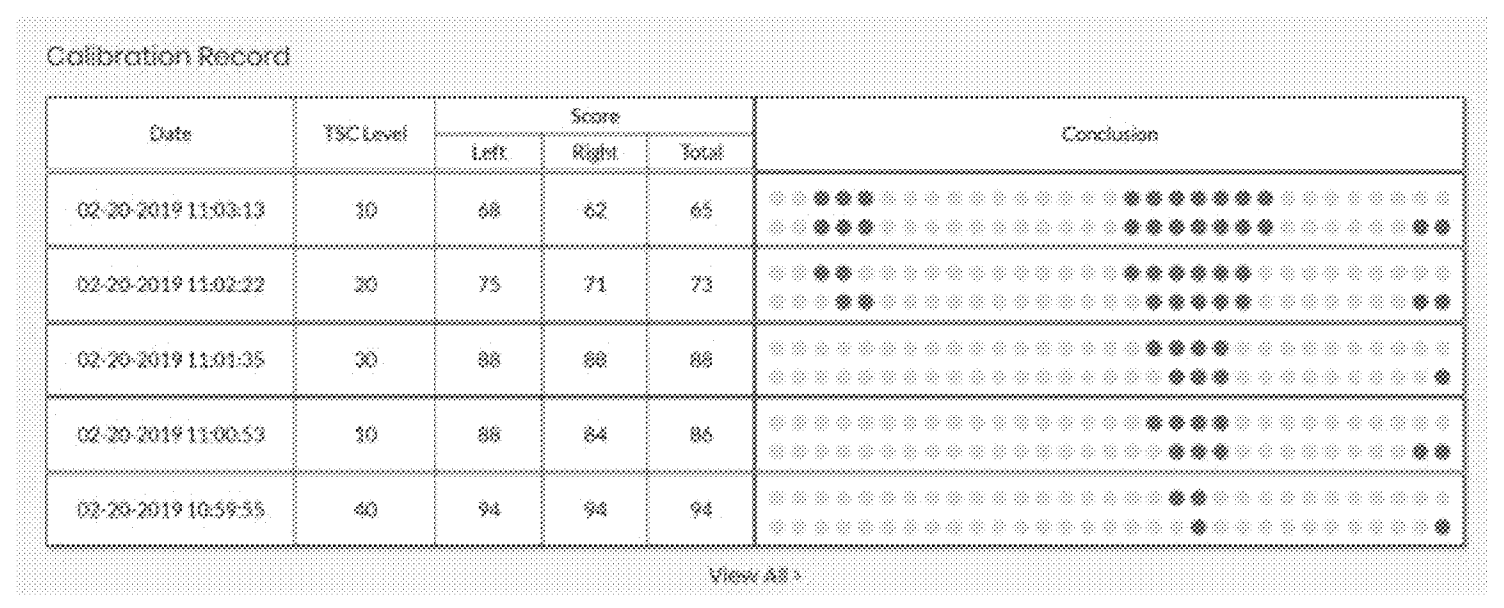
Figures 6, 7:
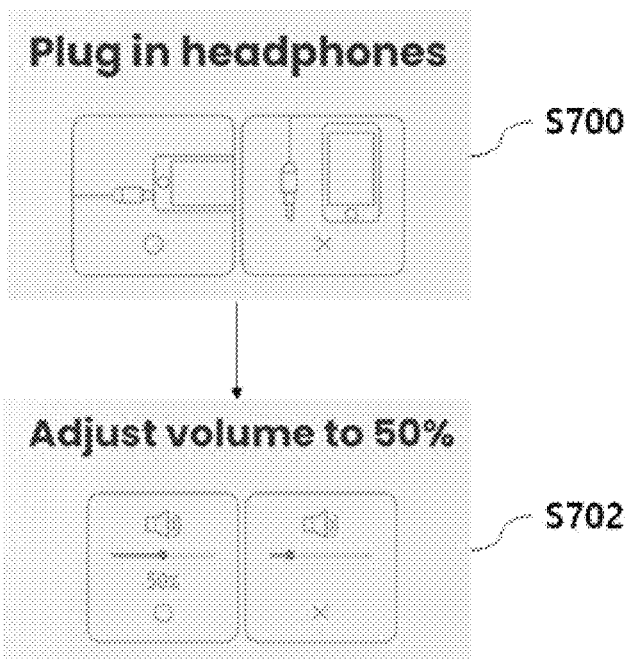
FIG. 6 is a diagram illustrating a result of providing the acoustic stimulation signals for stimulating the hair cells of cochlea according to the present embodiment.
FIG. 7 is a diagram illustrating a preliminary preparation process for hearing measurement according to the embodiment.

FIG. 5 is a diagram illustrating a hearing measurement result according to the present embodiment and FIG. 6 is a diagram illustrating a result of providing the acoustic stimulation signal for stimulating the hair cells of cochlea according to the present embodiment.

Hereinafter, a process of measuring and improving hearing according to the present embodiment will be described in detail with reference to the drawings.

FIG. 7 is a diagram illustrating a preliminary preparation process for hearing measurement according to the embodiment.

It is preferable that the hearing measurement according to the present embodiment is performed while wearing headphones and fixing the volume of the device.

Accordingly, as illustrated in FIG. 7, the apparatus according to the present embodiment checks whether the headphones are connected (step 700), and sets the volume to 50% (step 702).

Figure 8:
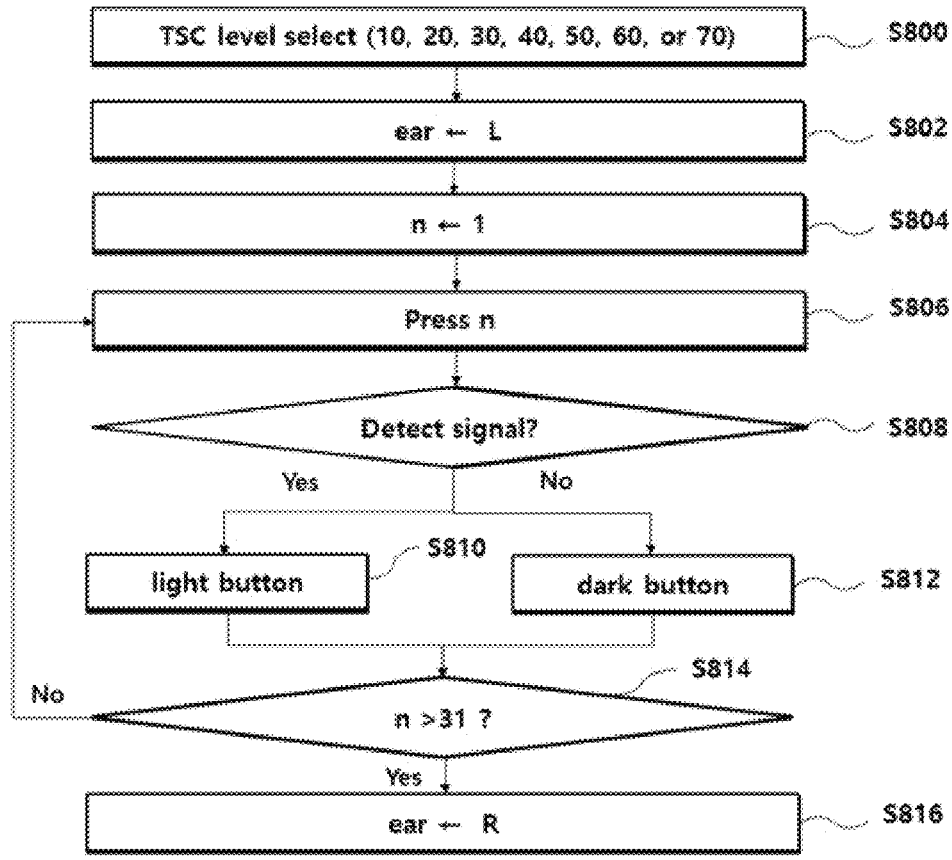
FIG. 8 is a diagram illustrating a process for measuring hearing according to the present embodiment.

FIG. 8 is a diagram illustrating a process for measuring hearing according to the present embodiment.

After the setting process as illustrated in FIG. 7 is completed, a hearing threshold is selected (step 800).

The hearing threshold according to the present embodiment may be selected as one of 10 to 70 decibels at 10 decibel intervals.

Basically, the left hearing is measured first (step 802), and the hearing measurement is sequentially performed from a frequency band corresponding to n=1 (steps 804 to 806).

The user determines whether or not the frequency band corresponding to button n to be currently measured is inaudible, and moves to the next frequency band when the acoustic signal is heard in the corresponding frequency band and selects the inaudible button 204 when the acoustic signal is not heard.

The apparatus according to the present embodiment determines whether or not the acoustic signal has been sensed through selection of the inaudible button 204 (step 808), changes the color of the button n to be currently measured from a first color to a second color (light) when the inaudible button 204 is not selected (step 810), and changes the color of the button n to a third color (dark) when the inaudible button 204 is selected (step 812).

Thereafter, the apparatus determines whether the measurement for all frequency bands has been completed (step 814), and measures the right hearing when the measurement is completed (step 816).

Figure 9:
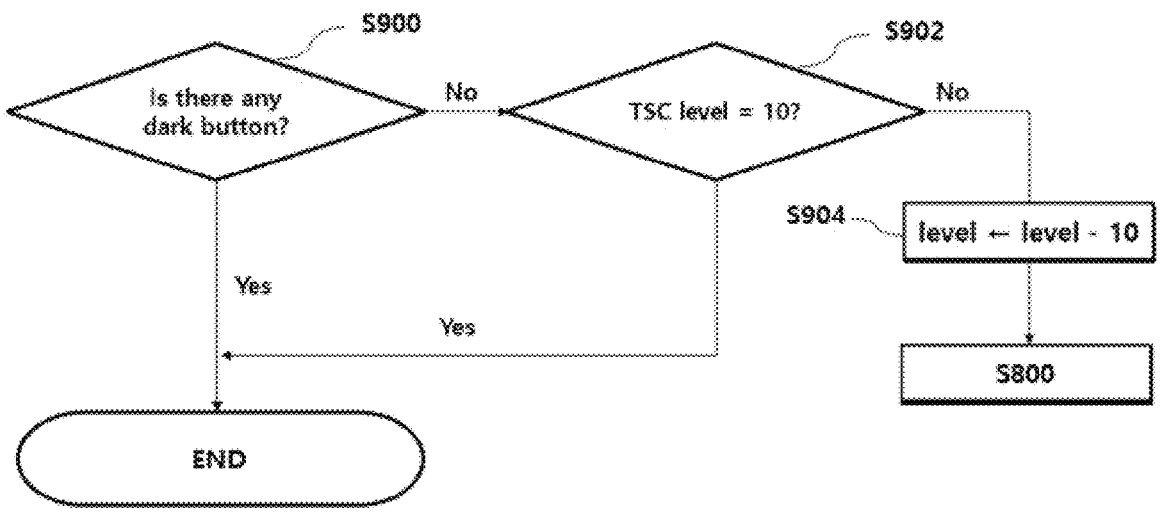
FIG. 9 is a diagram illustrating a process for adjusting a hearing threshold according to the present embodiment.

FIG. 9 is a diagram illustrating a process for adjusting a hearing threshold according to the present embodiment.

Referring to FIG. 9, after the left and right hearing measurement is completed through the process of FIG. 8, it is determined whether or not an inaudible frequency band exists (step 900).

Here, step 900 may be a process of determining whether a dark button corresponding to the third color exists.

If none of the inaudible frequency bands exist in the currently specified hearing threshold, the apparatus according to the present embodiment determines whether the current hearing threshold is a minimum value (10 decibels) (step 902).

If the specified hearing threshold is the minimum measurement value, the hearing measurement is terminated.

On the other hand, when the hearing threshold is not the minimum value, the hearing threshold is set lower by one level (step 904), and the hearing measurement of FIG. 8 is again performed.

That is, when the currently specified hearing threshold is 40 decibels and the inaudible frequency band is not detected at this hearing threshold, the hearing threshold is lowered to 30 decibels and the hearing measurement is performed again.

As described above, the embodiments of the present disclosure described above have been described for purposes of illustration, and it will be apparent to those skilled in the art that various modifications, additions, and substitutions are possible within the spirit and scope of the present invention and these modifications, changes, and additions should be considered as falling within the scope of the following claims.

What is claimed is:

1. An apparatus for hearing measurement based on a cochlear model comprising:
   a processor; and
   a memory connected to the processor,
   wherein the memory stores program instructions executable by the processor to output an interface in which n buttons corresponding to n frequency bands into which an audible frequency band is divided at 1/k octave resolution are arranged in a cochlear model,
   output acoustic signals corresponding to a predetermined hearing threshold in each of the n frequency bands,
   receive a user's input for whether each of the n frequency bands is inaudible at the predetermined hearing threshold, and
   output acoustic stimulation signals corresponding to the inaudible frequency band input by the user in predetermined sizes.

2. The apparatus for hearing measurement based on the cochlear model of claim 1, wherein the interface includes a hearing threshold button for selecting the hearing threshold, an inaudible button for selecting when an acoustic signal corresponding to the predetermined hearing threshold is not heard, and an activation button for outputting the acoustic stimulation signal.

3. The apparatus for hearing measurement based on the cochlear model of claim 1, wherein the hearing threshold is selected by the user or automatically selected according to a user's age.

4. The apparatus for hearing measurement based on the cochlear model of claim 2, wherein the program instructions control the buttons corresponding to the measured frequency band, the non-measured frequency band, and the inaudible frequency band to be displayed in different colors.

5. The apparatus for hearing measurement based on the cochlear model of claim 4, wherein the program instructions display the n buttons in a first color at the time of initial measurement, change a first button to a second color when the first button of the n buttons is selected, and changes the first button to a third color when the user selects the inaudible button while the acoustic signal in the frequency band corresponding to the first button is output.

6. The apparatus for hearing measurement based on the cochlear model of claim 4, wherein the program instructions output acoustic stimulation signals corresponding to first and m-th frequency bands among a plurality of m adjacent frequency bands to each other when the inaudible frequency band includes m adjacent frequency bands to each other.

7. The apparatus for hearing measurement based on the cochlear model of claim 1, wherein the acoustic stimulation signal has a size equal to or smaller than the hearing threshold provided at the time of measurement.

8. The apparatus for hearing measurement based on the cochlear model of claim 1, wherein the program instructions determine the number of buttons corresponding to the inaudible frequency band at the predetermined hearing threshold to change the predetermined hearing threshold to another hearing threshold.

9. A method for improving hearing in an apparatus including a processor and a memory connected to the processor, comprising:
   outputting an interface in which n buttons corresponding to n frequency bands into which an audible frequency band is divided at 1/k octave resolution are arranged in a cochlear model;
   outputting acoustic signals corresponding to a predetermined hearing threshold in each of the n frequency bands;
   receiving a user's input for whether each of the n frequency bands is inaudible at the predetermined hearing threshold; and
   outputting acoustic stimulation signals corresponding to the inaudible frequency band input by the user in predetermined sizes.

10. A non-transitory computer readable medium for performing the method of claim 9.

* * * * *